(12) United States Patent
Schwaibold et al.

(10) Patent No.: US 12,253,963 B2
(45) Date of Patent: *Mar. 18, 2025

(54) PRIORITIZATION OF INTERFACES OF A VENTILATOR

(71) Applicant: Loewenstein Medical Technology S.A., Luxembourg (LU)

(72) Inventors: Matthias Schwaibold, Karlsruhe (DE); Alexander Skiba, Stutensee (DE); Christof Schroeter, Karlsbad (DE); Mario Haushammer, Karlsruhe (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 18/483,741

(22) Filed: Oct. 10, 2023

(65) Prior Publication Data

US 2024/0045817 A1    Feb. 8, 2024

Related U.S. Application Data

(63) Continuation of application No. 17/444,957, filed on Aug. 12, 2021, now Pat. No. 11,822,495.

(30) Foreign Application Priority Data

Aug. 20, 2020    (DE) .................. 102020121835.4

(51) Int. Cl.
G06F 13/362    (2006.01)
G06F 13/42     (2006.01)
H04W 76/30     (2018.01)

(52) U.S. Cl.
CPC ........ G06F 13/362 (2013.01); G06F 13/4282 (2013.01); G06F 2213/0042 (2013.01); H04W 76/30 (2018.02)

(58) Field of Classification Search
CPC .............. G06F 13/362; G06F 13/4282; G06F 2213/0042; H04W 76/30; A61M 16/0051; A61M 16/0066; A61M 16/202; A61M 2016/0027; A61M 2016/0033; A61M 2205/3331; A61M 2205/3368; A61M 2205/3553; A61M 2205/3561;
(Continued)

(56) References Cited

U.S. PATENT DOCUMENTS 7,619,975 B1    11/2009  Lo
8,346,225 B2    1/2013   Raleigh
(Continued)

FOREIGN PATENT DOCUMENTS

WO    2016128280 A1    8/2016
WO    2021195336 A1    9/2021

Primary Examiner — Idriss N Alrobaye
Assistant Examiner — Henry W Yu
(74) Attorney, Agent, or Firm — Abel Schillinger, LLP

(57) ABSTRACT

A method for managing data exchange via at least three interfaces of a ventilator, at least one interface being configured for a data exchange with at least one counterpart station that is spatially separate from the ventilator. The data exchange comprises a data input and a data output, and a data output and/or data input is possible during an ongoing operation of the ventilator via at least one of the at least three interfaces only if it is determined that sufficient system resources and a reliable power supply are available.

20 Claims, 3 Drawing Sheets

(58) Field of Classification Search
CPC .. A61M 2205/3584; A61M 2205/3592; A61M 2205/502; A61M 2205/505; A61M 2205/52; A61M 2205/8206; A61M 16/024; G05B 19/0423
USPC .... 710/1, 7–8, 40, 44, 53, 62, 115, 244, 116
See application file for complete search history.

(56) References Cited

U.S. PATENT DOCUMENTS

| | | | |
|---|---|---|---|
| 10,025,351 B2 | 7/2018 | Ellis | |
| 2007/0195778 A1 | 8/2007 | Tatar | |
| 2009/0222138 A1 | 9/2009 | Boudreau | |
| 2010/0292544 A1* | 11/2010 | Sherman | A61M 16/101 128/204.23 |
| 2011/0002223 A1 | 1/2011 | Gross | |
| 2011/0197883 A1 | 8/2011 | McDaniel | |
| 2014/0000609 A1 | 1/2014 | Steinhauer | |
| 2018/0021534 A1* | 1/2018 | He | G06F 3/1423 128/204.21 |
| 2018/0228386 A1* | 8/2018 | McCall | G16H 50/20 |
| 2019/0073012 A1* | 3/2019 | Sultenfuss | H02J 7/0068 |
| 2021/0299376 A1 | 9/2021 | Gleim et al. | |

* cited by examiner

PRIORITIZATION OF INTERFACES OF A VENTILATOR

CROSS-REFERENCE TO RELATED APPLICATIONS

The present application is a continuation of application Ser. No. 17/444,957, filed Aug. 12, 2021, which claims priority under 35 U.S.C. § 119 of German Patent Application No. 102020121835.4, filed Aug. 20, 2020. The entire disclosures of these two applications are expressly incorporated by reference herein.

BACKGROUND OF THE INVENTION

1. Field of the Invention

The invention relates to a method for managing data exchange via interfaces of a ventilator.

2. Discussion of Background Information

Modern ventilators usually have a plurality of interfaces which enable inputs and a data exchange. Via the various interfaces, a ventilator can be set both directly at the ventilator, but also for example via an Internet connection, e.g. by way of remote maintenance. In present-day ventilators, here all the interfaces are released simultaneously in order for example to effect data inputs or else simultaneously to transfer a software update. If a plurality of data inputs via different interfaces are effected simultaneously, it may happen that these data inputs are not compatible with one another, e.g. for the purposes of a patient's therapy, and make application of the ventilator ineffective or even harmful. Even more extensive malfunctions of the apparatus cannot be ruled out, which may likewise result in the patient being affected in a harmful way.

In view of the foregoing, it would be advantageous to have available a method for safely controlling a ventilator. Consequently, the instant invention provides a method and the apparatus set forth in the instant independent claims. The dependent claims set forth advantageous embodiments of the claimed method and apparatus.

SUMMARY OF THE INVENTION

Specifically, the invention provides inter alia, a method for managing data exchange via at least three interfaces of a ventilator, wherein at least one interface is configured for a data exchange with at least one counterpart station that is spatially separate from the ventilator, wherein the data exchange comprises a data input and a data output, wherein a data input via one of the interfaces blocks the data input via at least one other interface. However, the data input can furthermore also be blocked for more than one other interface or even all other interfaces.

In some embodiments of the method, a data output is possible at any time during the ongoing operation of the ventilator and given sufficient system resources and a reliable power supply via at least one of the interfaces. However, a data output can indeed also be possible via a plurality or even all of the interfaces. A reliable power supply is present for example if the ventilator is connected to the local electrical grid or else a rechargeable battery or battery of the ventilator is sufficiently charged. A sufficient charge of the rechargeable battery can be present for example at more than 50% or 20% of the maximum charge. Even a charge of more than 10% of the maximum charge or more than 5% of the maximum charge can be regarded as sufficient charge of the rechargeable battery. Moreover, it is conceivable for example for the ventilator to be configured to determine the sufficient rechargeable battery charge on the basis of the type, duration and interface of the data output. In this regard, for short data outputs via interfaces that require little energy, a lower rechargeable battery charge may be regarded as sufficient by the ventilator. For longer data outputs and/or data outputs via interfaces with a higher energy demand, a different rechargeable battery charge may be taken as a sufficient basis. In this case, the system resources primarily comprise resources such as the processor capacity and main memory for example. By way of example, during ongoing operation, the processor may in part be utilized to capacity by the control of the ventilation pressure, such that the data output may overload the processor, which would in turn greatly jeopardize the safety of the therapy. In that case, for example, the system resources would be regarded as insufficient. Particularly when consideration is given to the available system resources, a data transfer can also be delayed, i.e. not effected immediately, but rather carried out at a later point in time. Thus, for example if insufficient system resources are available at a point in time at which a data output is intended to take place, no data output should take place. The data output can then be delayed, however, and take place as soon as sufficient system resource are available again.

In some embodiments of the method, a data input is possible at any time during the ongoing operation of the ventilator and given sufficient system resources and a reliable power supply via at least one of the interfaces. A reliable power supply is present for example if the ventilator is connected to the local electrical grid or else a rechargeable battery or battery of the ventilator is sufficiently charged. A sufficient charge of the rechargeable battery can be present for example at more than 50% or 20% of the maximum charge. Even a charge of more than 10% of the maximum charge or more than 5% of the maximum charge can be regarded as sufficient charge of the rechargeable battery. Moreover, it is conceivable for example for the ventilator to be configured to determine the sufficient rechargeable battery charge on the basis of the type, duration and interface of the data input. In this regard, for short data inputs via interfaces that require little energy, a lower rechargeable battery charge may be regarded as sufficient by the ventilator. For longer data inputs and/or data inputs via interfaces with a higher energy demand, a different rechargeable battery charge may be taken as a sufficient basis. In this case, the system resources primarily comprise resources such as the processor capacity and main memory for example. By way of example, during ongoing operation, the processor may in part be utilized to capacity by the control of the ventilation pressure, such that the data input may overload the processor, which would in turn greatly jeopardize the safety of the therapy. In that case, for example, the system resources would be regarded as insufficient. Particularly when consideration is given to the available system resources, a data transfer can also be delayed, i.e., not effected immediately, but rather carried out at a later point in time. Thus, for example if insufficient system resources are available at a point in time at which a data input is intended to take place, no data input should take place. The data input can then be delayed, however, and take place as soon as sufficient system resource are available again.

In some embodiments of the method, a priority is assigned to the interfaces and the data input via an interface with higher priority blocks the data input via at least one interface of lower priority. However, the data input can furthermore also be blocked for more than one interface of lower priority or even all interfaces of lower priority.

In some embodiments of the method, the data input via at least one interface of lower priority is blocked if the data input via interfaces of lower priority conflicts with the data input via the interface of higher priority. However, the data input can furthermore also be blocked for more than one interface of lower priority or even all interfaces of lower priority.

In some embodiments of the method, the data input for changing the therapy settings is blocked vis-à-vis at least one interface of lower priority if a data input for changing the therapy settings is effected via an interface of higher priority. However, the data input for changing the therapy settings can furthermore also be blocked for more than one interface of lower priority or even all interfaces of lower priority.

In some embodiments of the method, the ventilator comprises at least three different interfaces, wherein at least three of groups a to e are represented by said at least three interfaces:
  a. Wireless interfaces for large distances
  b. Wireless interfaces for small distances
  c. User interface
  d. Wired interfaces
  e. Interfaces for a storage medium.

In some embodiments of the method, the ventilator comprises at least five different interfaces, wherein the ventilator has at least one interface from each of groups a to e:
  a. Wireless interfaces for large distances
  b. Wireless interfaces for small distances
  c. User interface
  d. Wired interfaces
  e. Interfaces for a storage medium.

In some embodiments of the method, the ventilator comprises at least three different interfaces, wherein at least three of groups a to f are represented by said at least three interfaces:
  a. Wireless interfaces for large distances
  b. Wireless interfaces for small distances
  c. User interface
  d. Wired interfaces
  e. Interfaces for a storage medium
  f. Patient interface.

In some embodiments of the method, the ventilator comprises at least six different interfaces, wherein the ventilator has at least one interface from each of groups a to f:
  a. Wireless interfaces for large distances
  b. Wireless interfaces for small distances
  c. User interface
  d. Wired interfaces
  e. Interfaces for a storage medium
  f. Patient interface.

In some embodiments of the method, the wireless interfaces of the ventilator can be activated and deactivated.

In some embodiments of the method, one of the interfaces is a user interface at the ventilator, and the user interface is assigned the highest priority with regard to the data input.

In some embodiments of the method, substantially all data inputs via interfaces into the therapy apparatus are blocked during ongoing operation of the ventilator.

In some embodiments of the method, therapy-related data inputs are blocked during ongoing operation of the ventilator.

In some embodiments of the method, the priority assignment can be circumvented via at least one interface, such that data inputs via this interface are given preference over the data inputs even via interfaces of the highest priority. This possibility can also be extended to a plurality or all of the interfaces.

In some embodiments of the method, the priority of the interfaces is defined on the basis of the distance between the ventilator and the counterpart station.

In some embodiments of the method, for data input purposes, a data input mode is started and the starting of the data input mode via one interface blocks the starting of a data input mode via the other interfaces.

In some embodiments of the method, different data input modes are in each case started for different data inputs, wherein the starting of a data input mode via one interface blocks the starting of the same data input mode by another interface of lower priority.

In some embodiments of the method, the starting of a data input mode for a data input via other interfaces is blocked if the data input mode to be started via interfaces of lower priority conflicts with the data input mode of the data input via interfaces of higher priority.

In some embodiments of the method, the data input via an interface is interrupted and/or terminated by the beginning of a data input by an interface to which a higher priority is assigned.

In some embodiments of the method, the activation of functions and/or modes of operation of the ventilator blocks the data exchange via at least one interface. In alternative embodiments, the activation of functions and/or modes of operation can also have the effect that a plurality or else all of the interfaces are blocked.

In some embodiments of the method, the activation of functions and/or modes of operation of the ventilator deactivates at least one interface until the end of the function and/or mode of operation. In alternative embodiments, the activation of functions and/or modes of operation can also have the effect that a plurality or else all of the interfaces are deactivated.

In some embodiments of the method, specific data inputs via an interface must be confirmed via an interface of higher priority. These specific actions and/or data inputs can concern for example critical and/or sensitive aspects of the patient and/or of the therapy. By way of example, that should also be understood to include switching of the ventilator from non-ongoing operation to ongoing operation, or vice versa. Changes in the therapy settings must also be confirmed via an interface of higher priority, if appropriate. Alternatively or supplementarily, it can be provided that apparatus updates, that is to say software and/or firmware updates, must likewise be confirmed via an interface of higher priority.

In some embodiments of the method, specific data inputs are not interrupted and/or terminated independently of the priority of the interface via which the data input is effected.

In some embodiments of the method, a message is generated by data inputs and/or data outputs via an interface, said message being output via at least one interface of higher priority.

In some embodiments of the method, the message persists for the duration of the data input.

In some embodiments of the method, the message persists after the data input and must optionally be confirmed via the interface via which the message is output.

In some embodiments of the method, after the data input via an interface, a message is generated and is output via at least one interface of higher priority, wherein the message contains a summary of the data input effected.

In some embodiments of the method, a criterion according to which the priority is assigned to the interfaces is based on the connection of the interface to the spatially separate counterpart station.

In some embodiments of the method, the priority is automatically assigned to the interfaces.

In some embodiments of the method, the priority of the interfaces is able to be varied manually at the ventilator.

In some embodiments of the method, the constituent parts and components of the ventilator are divided into modules and/or module groups, wherein the data input via one interface blocks only the affected module and/or the affected module group vis à vis data inputs via other interfaces.

In some embodiments of the method, the priority of the interfaces is allocated differently at least for ongoing operation and non-ongoing operation.

In some embodiments of the method, one of the interfaces is embodied as a USB interface and the ventilator does not transition to ongoing operation in the case of an active connection via said USB interface.

In some embodiments of the method, the USB interface of the ventilator is deactivated during ongoing operation.

In some embodiments of the method, the ventilator transitions from ongoing operation to non-ongoing operation as soon as a connection via the USB interface is established.

In some embodiments of the invention, a data input via all other interfaces is blocked when a connection via the USB interface is established.

In some embodiments of the method, all interfaces are blocked at least at times vis à vis therapy-related inputs at the ventilator after a therapy-related input via an interface has been concluded.

In some embodiments of the method, a change in the ventilator from ongoing to non-ongoing operation, or vice versa, is blocked at least at times via all interfaces after such a change has been made.

In some embodiments of the method, a data input via all interfaces, in particular via the user interface, is blocked while the ventilator processes data recorded during ongoing operation.

In some embodiments of the method, the data input via all interfaces is substantially blocked if a serious fault is registered by the ventilator and/or the firmware of the ventilator. Technical faults, in particular, may be regarded as such serious faults. Defective sensors or defective electronics should be taken into consideration here, for example.

In some embodiments of the method, substantially all wireless connections via corresponding interfaces of the ventilator are terminated and the interfaces for wireless connections are deactivated if the ventilator transitions and/or is intended to transition to ongoing operation.

In some embodiments of the invention, the ventilator does not transition to ongoing operation until all wireless connections are interrupted and the interfaces for wireless connections are deactivated.

In some embodiments of the method, specific actions and/or data inputs via the user interface are always possible independently of the prioritization.

The ventilator provided by the invention comprises at least three interfaces for a data exchange, wherein at least one interface is configured for a data exchange with at least one counterpart station that is spatially separate from the ventilator, wherein the data exchange comprises a data input and a data output, wherein a data input via the interface blocks the data input via at least one other interface. However, the data input can furthermore also be blocked for more than one other interface or even all other interfaces.

In some embodiments of the ventilator, a data output is possible at any time during the ongoing operation of the ventilator and given sufficient system resources and a reliable power supply via at least one of the interfaces.

In some embodiments of the ventilator, a priority is assigned to the interfaces and the data input via an interface with higher priority blocks the data input via at least one interface of lower priority. However, the data input can furthermore also be blocked for more than one interface of lower priority or even all interfaces of lower priority.

In some embodiments of the ventilator, the ventilator comprises at least three different interfaces, wherein at least three of groups a to e are represented by said at least three interfaces:
  a. Wireless interfaces for large distances
  b. Wireless interfaces for small distances
  c. User interface
  d. Wired interfaces
  e. Interfaces for a storage medium.

It should be pointed out that the features presented individually in the claims can be combined with one another in any technically expedient way and demonstrate further configurations of the invention. The description additionally characterizes and specifies the invention in particular in association with the figures.

It should furthermore be pointed out that any conjunction "and/or" which is used herein, appears between two features and interlinks them should always be interpreted such that only the first feature may be present in a first configuration of the subject matter according to the invention, only the second feature may be present in a second configuration and both the first feature and the second feature may be present in a third configuration.

A ventilator should be understood to mean any apparatus which supports a user or patient with regard to natural breathing, performs ventilation of the user or patient and/or serves for respiratory therapy and/or influences the breathing of the user or patient in some other way. It includes, for example, but not exclusively, CPAP and BiPAP apparatuses, narcosis or anesthesia apparatus, respiratory therapy apparatuses, (clinical, extra clinical or emergency) ventilators, high-flow therapy apparatuses and cough assist machines. Ventilators can also be understood as diagnosis apparatuses for ventilation. In this case, diagnosis apparatuses can generally be used for detecting medical parameters of a patient. They also include apparatuses which can detect and optionally process medical parameters of patients in combination with or exclusively concerning breathing.

An interface should be understood in the broadest sense as any type of device for connection—independently of the type of connection—between the ventilator and a counterpart station or a person. In this case, an interface for a connection between the ventilator and a person may be a user interface, for example, which enables the interaction between person and ventilator directly at the ventilator.

A patient interface, unless expressly described otherwise, can be understood to mean any part or connected peripherals of the ventilator intended for interaction, in particular for therapy or diagnosis purposes, with a patient. In particular, a patient interface can be understood as a mask of a ventilator or a mask connected to a ventilator. Said mask can be a full-face mask, i.e. a mask enclosing nose and mouth, or a nasal mask, i.e. a mask enclosing only the nose. Tracheal tubes and so-called nasal cannulas can also be regarded as a mask.

The individual constituent parts of the ventilator can be subdivided into modules, wherein the entire ventilator can also be understood as a single module. The module can be defined from various standpoints, which will not be explained in more specific detail at this juncture and have no influence on the invention as such. Overlapping of different modules by the constituent parts of the ventilator is also possible here. In this regard, a constituent part can be assigned to two modules, for example. Furthermore, the individual modules can also be combined to form module groups, wherein said module groups can also have overlaps, under certain circumstances.

The source of a data input can have various forms, but generally results at least indirectly in an electrical signal which can be processed within the ventilator. By way of example, the data input can be effected mechanically via a user interface in the form of a touch-sensitive screen. Via the touch-sensitive screen, the mechanical touch is converted into an electrical signal which can be processed in the ventilator. However, by way of example, an electrical signal can also be input directly via other interfaces. A precise description of all possible ways of effecting a data input at the ventilator or communicating it via an interface will be dispensed with at this juncture since the form of the data input is of no relevance to the inventive method or the inventive apparatus.

In the case of the ventilator, a distinction can be drawn substantially between ongoing operation and non-ongoing operation. In this case, unless explicitly indicated otherwise, ongoing operation means the use of the ventilator on a patient, for example. In the case of therapy apparatuses, this may be for example an active therapy carried out on a patient. If the ventilator is designed as a respiratory therapy apparatus, for example, then the respiratory therapy apparatus is in ongoing operation when the patient is connected to the respiratory therapy apparatus and a therapy program is running, that is to say that the patient is being ventilated or supported with regard to breathing. If the ventilator is a diagnosis apparatus, for example, then ongoing operation is the use of the diagnosis apparatus for making a diagnosis on a patient, for example, or the recording of data for diagnosis. The ventilator is in non-ongoing operation when the ventilator is not being actively used. This may therefore be the case, for example, when the ventilator is in a standby mode, a so-called "sleep" mode or else in the switched-off state— irrespective of whether or not there is an electrical power connection.

Unless explicitly indicated otherwise, a counterpart station that is spatially separate from the ventilator describes a counterpart station which is not necessarily permanently connected to the ventilator electrically and/or mechanically and also does not have to be permanently connected to the ventilator as an essential requirement for operation. By way of example, a spatially separate counterpart station can also be understood to mean wired apparatuses or else storage media, such as, for example, feeders, USB sticks, etc., even though these can be or are directly spatially connected to the ventilator at least at times.

The priority of the interfaces can be determined and set on the basis of a wide variety of aspects. One possibility of priority allocation can be effected manually, for example, such that the user can quite freely allocate the priority of the interfaces. The highest priority can be assigned permanently and optionally invariably to the user interface, in particular, which enables inter alia a data input directly at the ventilator. Besides the allocation of the highest priority to the user interface, it is also possible to allocate the highest priority to specific interfaces, such as service interfaces, for example. If service counterpart stations and/or counterpart stations of a test bed share the interface with other counterpart stations, then a counterpart station-dependent priority is also conceivable for these interfaces. By way of example, these interfaces can also be managed doubly in the priority assignment, such that an additional feature is noted with respect to the priority assignment. A further possibility of enabling the data input under the highest priority—i.e., even above the user interface—for possible counterpart stations of a test bed or service counterpart stations can be implemented in the form of bypassing or overwriting or bridging of the priority by the counterpart stations. To that end, for example, the communication of a bridging command by the respective counterpart station would also be possible, such that the ventilator recognizes that the priority order is intended to be deactivated and/or an increased (the highest) priority is intended to be assigned temporarily to the transmitting counterpart station. Besides the manual allocation, the priorities can also be defined automatically. In this case, it is possible to define various criteria according to which the priority is allocated.

Moreover, a different priority allocation is possible, for example, depending on whether the ventilator is in ongoing operation or non-ongoing operation. Another possibility for differentiating between ongoing operation and non-ongoing operation can be configured for example such that in principle the highest priority is assigned to ongoing operation. In some embodiments, therefore, ongoing operation also cannot be terminated, or can be terminated only under specific prerequisites—such as, for example, a malfunction of the ventilator. Such malfunctions may for example reside in the actual functioning but may also be caused by defective peripherals and/or sensors. If, by way of example, the data input by sensors of the ventilator or sensors connected to the ventilator stops during ongoing operation, then the ventilator can inter alia assume a malfunction and thereupon end ongoing operation.

By way of example, the priority can be defined on the basis of a distance between ventilator and counterpart station. In this case, the pure physical distance is a secondary criterion, or criterion that may be disregarded, but can indeed be used as a criterion for the priority in further embodiments. By way of example, the maximum distance between ventilator and counterpart station can be used as a main criterion for the assignment of the priority to interfaces. Consequently, from this standpoint, the highest priority would be assigned to a user interface directly at the ventilator. According to this criterion, higher priorities with regard to the data input can likewise be assigned to interfaces for short distances, for example for wireless connections such as Bluetooth or other WPAN connections (Wireless Personal Area Network) or else short-range radio connections. The next lower level of the priorities can then be assigned for example to the interfaces for connections in the building in which the ventilator is used. They can include for example a remote control in a sleep laboratory, but also for example a central station in a clinic. Further examples of this type of interfaces can serve for example for read-out of detailed therapy data, a connection to diagnosis apparatuses (PSG), for external connection of a radio module, general service, communication with a test bed or firmware updates. According to the priority allocation explained by way of example, no priorities are assigned to interfaces for connections over large distances, such as e.g. connections to the Internet or mobile radio. For interfaces for storage media such as memory cards or USB sticks, an exception regulation can be implemented, for example, according to which for example the lowest priority is allocated to precisely those interfaces for storage media. Furthermore, however, the categorization with a high priority, in some cases even higher than the priority of the user interface, is also conceivable.

Another method or criterion for defining the priority of interfaces may for example also include the stability or quality of the connection of the interface. By way of example, the priority of different interfaces of the same type, such as for example, interfaces for connection over large distances (e.g., via wire/LAN, Wi-Fi/WLAN, mobile radio to the Internet), can thus be differentiated further. If the ventilator is connected to the Internet for example via a wired interface stably and with high transmission quality and at the same time via a different interface there is a connection by mobile radio, but it is rather unstable or has low transmission quality, the mobile radio interface can be assigned a lower priority than the wired interface.

In one exemplary embodiment of the invention, therefore, the priority of the wireless interfaces is determined automatically on the basis of the connection quality. By way of example, if one interface has a wireless connection to the mobile radio Internet with poor quality (for example in the form of the transmission speed or connection stability), and at the same time if another interface has a connection to the Internet via WLAN with better transmission speed and stability than the mobile radio connection, the interface with connection via WLAN can be assigned a higher priority automatically or else manually. The same can moreover also additionally apply to wired connections. By way of example, if an external control unit is connected to an interface via a cable, this connection can be assigned a higher priority with regard to inputs. In addition to the priority, it is also conceivable that interfaces which have the same connection destination—e.g. the Internet—can be switched (automatically or manually) so that a connection is established only via one of the interfaces in each case. In this regard, by way of example, in a ventilator having a mobile radio interface, a WLAN/Wi-fi interface and also a wired interface for LAN/Internet connections, it is possible to activate only the best quality in each case. By way of example, if the Wi-fi connection is poor or very susceptible to interference and a wired connection is not present, the connection via the mobile radio interface can be given preference and be the sole connection activated.

The priority can be represented in a ranking list, for example, in which the interfaces are ordered according to the envisaged priority. In some embodiments, the prioritization of the interfaces can also follow a points system. In this regard, a number of points can be calculated for each interface on the basis of a wide variety of criteria and optionally also an assessment of the respective criteria. By way of example, a higher number of points may result in a higher priority. Besides fixedly allocated priorities, a dynamic allocation of the priorities for the interfaces is also conceivable. In some embodiments, moreover, the possibility is also provided that the priority can be adapted to a certain extent or totally freely via the user interface or else other interfaces.

In some exemplary embodiments, the highest priority can be assigned to an interface for wired connections, such as a USB interface, for example, such that this priority is still above ongoing operation. In this regard, a connection set-up via a USB interface can indeed have the effect that ongoing operation is interrupted or terminated or ended. In some embodiments, the priority of the interfaces can also be correspondingly adapted dynamically, wherein the priority is then based on the counterpart station connected to the interface. By way of example, if an empty SD memory card is connected to a correspondingly embodied interface, then this may result in a lower priority than if, for example, an SD memory card with a master configuration is connected to the interface. If such a priority allocation is provided, then for example the content of the SD card or of the USB stick is firstly scanned without a concrete data input being performed. If it is ascertained in the process that the priority of the USB stick or the SD card is intended to be assigned an, at least temporarily, very high priority or the highest priority—for instance in the form of a corresponding instruction contained on the USB stick or the SD card—then the corresponding interface is initially assigned the high priority, which also results in a high priority for the data input via the corresponding interface.

In some embodiments, the data input via other interfaces is blocked, independently of whether an interface via which a data input is intended to be begun is assigned a higher priority. This may indeed also concern only specific actions or data inputs, for example. By way of example, a configuration of the ventilator via a storage medium may have the effect that a data input in the sense of a configuration via other interfaces—for example of a network connection—is blocked.

If a data input is very generally performed via one of the interfaces of the ventilator, then the data input via other interfaces is blocked, such that data inputs are only ever possible via one interface. By way of example, the ventilator can alternatively also be configured such that in the case of a data input via one interface, specific data inputs via other interfaces are still possible. By way of example, only the constituent parts of the ventilator that are affected by the data input may be blocked vis-à-vis data inputs via other interfaces.

In the case of some data inputs, moreover, provision is made for example for waiting for the changeover from ongoing operation to non-ongoing operation of the ventilator. By way of example, if a data input in the sense of a configuration change is intended to be effected, then this cannot be performed until ongoing operation has ended. By way of example, during ongoing operation, a storage medium with a new configuration can be connected to the ventilator via an interface, but this configuration will be transferred to the ventilator or installed at the earliest after the end of ongoing operation. On the other hand, a changeover to ongoing operation can also be prevented as long as data inputs via interfaces, such as the transfer of a configuration, for example, are effected. If the ventilator has a kind of automatic start function which changes the ventilator over to ongoing operation if a use of the ventilator is intended to be begun or is begun, this function can also be blocked during data inputs. Such an automatic start function can be initiated for example by a peripheral device being attached to the patient or—on the basis of the example of a ventilator—the beginning of the patient's breathing into the apparatus or using the apparatus via a patient interface (mask). In alternative embodiments, it is also possible, conversely, for any data input to be ended or terminated and also for at least some interfaces to be blocked if the ventilator transitions to ongoing operation by way of the automatic start function. In other words, for example, if the patient breathes into the mask or uses the mask of the ventilator, then the apparatus interrupts at least some data inputs and/or transfers and blocks at least some interfaces—in particular wireless interfaces for large distances—for data inputs. In some embodiments, therefore, a patient interface—e.g., in the form of a mask (ventilation mask, but also types of tracheal tubes or nasal cannulas)—can also be included among the interfaces of the ventilator. In that case, patient interfaces can constitute a further group f of interfaces which must be represented at least once or from which at least a selection is made.

In order to block data inputs via other interfaces while a data input is already being effected via one interface, there are a number of conceivable possibilities. One of the possibilities may consist for example in the interfaces that are not used for this input generally being blocked for inputs of data inputs. In this regard, the system can be configured for example such that the remote counterpart stations are not even enabled to contact the interface in the first place or else all inputs via the interface are not forwarded, but rather discarded directly after reception/arrival at the interface. A further possibility consists in not blocking in principle all interfaces with regard to a data input, but rather only the components affected by the data input.

Furthermore, by way of example, a control unit can also be designed to block or to enable the data input via interfaces. In this regard, under given circumstances, a data input in the direction of the ventilator may always be possible, but on the basis of the priority the control unit decides whether this data input is accepted, forwarded and/or stored. For wireless interfaces for large distances, such a circumstance may not be manifested, for example, if the ventilator is in ongoing operation and therefore precisely those interfaces are deactivated, i.e. are not reachable at all for data inputs.

The priority of the interfaces plays a part particularly when data inputs are performed generally at the ventilator. If a data input via an interface of a medium priority is performed, then at least the component at which the data input is performed is blocked vis à vis changes/data inputs via at least one interface of lower priority. However, it can also be blocked vis à vis more than one interface of lower priority or even all interfaces of lower priority. A data input is generally possible for example only if there is no data input via another interface. By way of example, it may also be possible that, in the case of a data input, the ventilator is blocked only vis à vis interfaces which have a lower priority than the interface via which the current data input is being performed. For example, if a data input via an interface of higher priority is intended to be effected, then the present data input is interrupted or paused, if appropriate, and the data input via the interface of higher priority is begun. In this case, the process of interrupting the data input via the interface of lower priority may take some time, i.e., a number of seconds to minutes. If the intention is to begin a data input or to start a data input mode via an interface of higher priority, then the interface of higher priority remains blocked until the data input or the data input mode via the interface of lower priority has been interrupted or ended, if appropriate. During this time period, a message giving information about the process of interruption that is under way can be passed to the counterpart station of the interface of higher priority. The fact of whether the data input via the interface having lower priority in each case is interrupted or paused or even possibly firstly brought to an end before data inputs can be effected via the interface of higher priority may for example also depend on the respective data input. A direct prioritization of the respective data input is likewise conceivable here, but can also follow a simple logic, for example, according to which data inputs are marked with "permitted to be terminated" or "not permitted to be terminated". In this regard, for example, ongoing firmware updates can be provided with a marking that they are not permitted to be terminated, since a termination of the update may possibly result in loss of data or damage at the ventilator.

In some embodiments, the data input via the interface of lower priority is interrupted as soon as a data input via an interface of higher priority is activated, even if concrete data inputs are not yet effected. In some embodiments, this means for example that touching or activating the user interface can result in the data inputs via other interfaces being interrupted. In some embodiments, however, the data input via interfaces of lower priority is actually only interrupted if a concrete data input via an interface is begun. Furthermore, it is also conceivable that a data input mode must be activated before the actual data input. In this regard, a connection between ventilator and counterpart station via an interface of higher priority can be set up or activated without a data input via the interface of lower priority being interrupted. The interruption only ensues if a concrete data input is intended to be begun as a result of the activation of a data input mode via the interface of higher priority.

In some embodiments, the data input can also be blocked or raised on the basis of the type of data input. Moreover, it is conceivable for any specific types of data inputs to come under the handling of the priority. In this regard, by way of example, the blocking—associated with the priority—of the data input via interfaces other than the currently active interface can prevent data inputs from being performed which bring about different, possibly even opposing, effects.

Moreover, some types of data inputs, for instance the data transfer from sensors, can be totally excluded from the priority treatment or these data inputs are allowed not to be terminated if a data input via an interface of higher priority is started.

Specific actions or data inputs via the user interface can also be excluded from the priority treatment, such that specific data inputs are always enabled via the user interface. This relates in particular to menu control or else the confirmation/activation of specific processes and/or data inputs via other interfaces.

In some exemplary embodiments, the interfaces are connected to a control unit which differentiates whether the input received via the interface constitutes a permissible data input and, on the basis thereof, allows or blocks a connection between interface and ventilator or one of the constituent parts (e.g., modules, module groups). To that end, the control unit has access to the priority assignment of the interfaces or the priorities are stored in the control unit. On the basis of various criteria, the control unit can then decide whether and/or via what interface a data input or the start of a data input mode is allowed and can be carried out.

In some exemplary embodiments, not only the priority of the interface and whether a data input is taking place via it determine whether an access via an interface—that is to say a data input, but also the read-out of data (the data output)—is possible, but also whether for example a ventilation therapy is currently being carried out and the ventilator is being used on a patient. If the ventilator is actively in use on a patient, that is to stay in ongoing operation, then for example some interfaces can generally be blocked. As a result, it is possible for example to prevent danger during therapy as a result of radio radiation, overloading of the processor or as a result of a restart of the apparatus. The transfer of a firmware update can constitute a further source of danger. This can for example also result in a changed mode of operation of the processor, which can in turn have a negative effect on the function of the ventilator. Therefore, the system can be configured, for example, such that while the ventilator is being used on the patient, some interfaces can be completely blocked for access to the ventilator, i.e. including for the read-out of data. Critical interfaces such as for mobile radio connections and/or wireless Internet/WLAN connections, inter alia, should be taken into consideration here. Less critical interfaces, such as, for example, WPAN connections (Bluetooth), or network connections for a remote control in sleep laboratories, for example, can in this case be excluded from the general block. In an alternative embodiment, by way of example, individual components can also be blocked vis à vis data inputs or interfaces. In this regard, by way of example, it is possible to block a data input by the remote monitoring or telemonitoring during the therapy, while read-out of the data remains possible.

By way of example, in some embodiments, it is possible that the beginning of a data input via interfaces of higher priority can interrupt and/or terminate any data input via interfaces of lower priority. Furthermore, in further exemplary embodiments it is possible for the entire access via the interface of lower priority to the ventilator to be interrupted and/or terminated. Depending on the present data input via the interface of lower priority, this interruption and/or the termination can last for a few seconds to a number of minutes during which the interruption is initiated. In this waiting time, the interface having higher priority may initially still be denied access until the interruption of the previous data input via the interface of lower priority has been carried out. In some cases, the interruption may for example not actually be initiated, i.e. the data input via the interface of lower priority may not be interrupted or terminated, even though the interface with the more recent request for an access and/or data input is assigned a higher priority. This may be the case for example if a firmware update is being transferred via an interface of lower priority. In such a case, it would be necessary to wait for the data input of the interface of lower priority to be completed before the data input via the interface of higher priority can be begun. To that end, for example, there may be an additional priority management for an individual data input. Another possibility may also be for example the allocation of markings to the individual data input which can be taken as a basis for deciding whether an interruption or a termination is allowed if a more recent data input via an interface of higher priority is intended to be begun.

One exemplary embodiment comprises a confirmation of accesses and/or data inputs and/or specific actions via one interface to the ventilator via another interface. By way of example, if a firmware update is intended to be transferred to the ventilator or a module via an interface for Internet or network connections (remote monitoring/telemonitoring/remote maintenance), it may accordingly be necessary for this type of data input to be confirmed and/or accepted for example via the user interface at the ventilator. The priority of the interfaces can be taken into account in the confirmation as well. In this regard, the system may be configured for example such that individual data inputs via an interface must be confirmed by an interface of higher priority. In this case, a decision can also be taken as to whether all interfaces of higher priority can be used to confirm the data input or else an access generally. By way of example. a confirmation is requested via all active interfaces having a higher priority than the interface via which an access is intended to be effected. In this case, by way of example, the confirmation via one of the interfaces is already sufficient for the access to be allowed. Alternatively, it is also conceivable for a confirmation of specific accesses to be possible only via the interface or interfaces of highest priority. These actions, data inputs and/or accesses may include for example sensitive data such as patient information. A change in the therapy data and/or therapy settings may also require a confirmation via another interface, optionally an interface of higher priority. Alternatively or supplementarily, provision can be made for a data output via an interface at least partly to require the release and/or confirmation via an interface of higher priority. By way of example, if sensitive data are intended to be accessed via a remote access, for instance via a wireless interface, provision can be made for a confirmation of the data exchange or of the data output to be requested via the user interface.

Furthermore, the release of accesses can also be used to enable a simultaneous data input via two interfaces. By way of example, if a data input via an interface of high priority takes place and the intention is likewise to begin a data input via an interface of lower priority, then a release for the interface of lower priority can be granted via the interface of higher priority. This release can for example also encompass only very narrow bounds, for example only individual constituent parts of the ventilator, in order that the data input via the interface of higher priority is not influenced, for example.

By displaying information or a message concerning accesses for example for the purpose of data input/data output via respective interfaces to the ventilator, it is possible to generate and display information or a message to other interfaces, in particular to interfaces of high priority and in this case particularly to the user interface at the ventilator. In a further embodiment, however, such information or such a message is generated only if the ventilator is not being actively used on a patient, i.e. is in non-ongoing operation. If a data input/data output takes place during ongoing operation, information or a message about that can also be stored and be displayed after the end of ongoing operation. In this case, the information or message can be displayed for example at the beginning of the access, but can also be displayed during the entire access. Furthermore, display after access has taken place or after the data input is also conceivable. The display of the message can for example persist for a specific period of time after the access and then be automatically masked out. A request for confirmation of the information about the access can also be implemented. By way of example, outside application of the therapy, a data input via an interface can be effected, whereupon a message is generated and displayed at the ventilator for example for the user interface. The user at the ventilator has the possibility there of noticing this message and confirming the message. In the case of a message duration which is intended to last over the entire data input, the message, possibly also in a modified embodiment, can be displayed permanently via the user interface. Alternatively or additionally, after the conclusion of the data input, a (further) message can be forwarded to the user interface. This message can for example also contain a summary or overview of the changes as a result of the data input. The message can contain information about the connected or active interfaces, interfaces via which a data exchange (data input and/or data output) is effected, the content of the data exchange, the duration of the data exchange, currently blocked and/or non-blocked interfaces and/or else whether the ventilator is in ongoing operation. Further details about active data inputs, data outputs and interfaces can also be represented in a message.

A data output should be possible at any time, also independently of the blocking of data inputs, via at least one or at least two interfaces. If the data input via an interface is not possible, the data output via this interface need not simultaneously be blocked, however. That is to say that via the interface a data output to the counterpart station can be effected, but a data input from the remote counterpart station cannot be effected. In this case, the possibility of outputting data should be understood to mean that this is intended to be possible, but need not necessarily actually be effected. That is to say that data need not be read out via at least one or at least two interfaces at all times. In this regard, at one time data may not actually be read out at all.

In some embodiments, however, the data output can also be blocked under specific circumstances. In this regard, an excessively large number of active connections via the interfaces for data output (also conceivable for a data input) may overload the system resources, such as e.g. processor capacity, data bus capacity, main memory, etc. In order to prevent this, the data output via at least one interface or some interfaces can be blocked. For some applications of the ventilator, for example in a sleep laboratory where the ventilator is exclusively remote-controlled, it may be expedient for data outputs and data inputs to be activated only via the remote control. In this regard, for example, the user interface in the form of a (touch-sensitive) screen can remain switched off in order that the patient can sleep.

During the data output, for example, if the data of the ventilator that are recorded during ongoing operation are transmitted to a counterpart station, it may likewise be expedient to block other data inputs and data outputs during the transfer, in order that the processor capacity is fully available for e.g., encryption of the data.

Moreover, provision can be made for the priority of the interface to be assigned on the basis of the process and/or the action, for example the type of data input, and/or for a priority to be assigned according to users at the interface. By way of example, the priority of the interface via which a medical attendant/physician effects a data input can be assigned a higher priority than the interface via which the user/patient of the ventilator effects a data input. In the case of identical interfaces, too, for example a wireless interface via which both patient and medical attendant/physician can effect data inputs, prioritization can be carried out depending on user. For example, provision can be made for a wireless interface via which a medical attendant/physician effects a data input to acquire a higher priority than if the patient intends to effect a data input and/or data output via the wireless interface. Moreover, the interface via which a medical attendant/physician or else a service technician connects to the ventilator can be assigned a higher priority than for example the user interface via which the patient accesses the ventilator.

A process which can be assigned a particularly high priority, for example, such that the interface via which the process is effected is likewise assigned an increased priority, is for example a service process such as the transfer or installation of firmware. The priority of a service process can for example even lie above the priority of the user interface at the ventilator. The priority of the interfaces can thus be variable in the form that a process, for example a data input or the type of data input, crucially influences the priority of the interface. A process of particularly high priority may be for example the switchover from non-ongoing operation to ongoing operation. If the patient is starting his/her therapy, for example, i.e. would like to switch the ventilator to ongoing operation, this action/process can result in a higher priority than for example a data exchange of a medical attendant/physician via a wireless interface, even if the latter, on account of the use by the medical attendant/physician, should actually acquire a higher priority than the interface via which the patient/user acts.

Moreover, certain processes can cause interfaces to be at least partly blocked. In this regard, besides a transition between ongoing and non-ongoing operation, further processes can also cause at least some of the interfaces to be blocked at times. These processes may be boot-up (e.g., starting/start-up of the apparatus), initialization of parts of the electronics, e.g., including interface modules, firmware update, processing of data, self-test, virus scan and initiation of a shutdown (switch-off of the apparatus). In particular the change in an operating state, such as, for example, the switchover between ongoing and non-ongoing operation and/or the switch-on of the ventilator and/or the switch-off of the ventilator, can cause some or all of the interfaces to be blocked at least at times or temporarily.

The inventive ventilator has for example at least three interfaces, in some embodiments also at least four or five interfaces. If the ventilator has at least five interfaces, each of the following groups a, b, c, d, e should be represented by at least one interface:

a. wireless interface for large distances (mobile radio) for example for telemonitoring, teleservice, telesetting, FW update b. wireless interface for small distances (Bluetooth, WPAN), for example for remote control via app, feedback concerning therapy in app, service processes; connection to diagnosis apparatuses (polygraphy), FW update/firmware update c. user interface (user interface, GUI) for example for operator control, feedback, service d. wired interfaces for example for remote control in a sleep laboratory, read-out of detailed therapy data, connection to diagnosis apparatuses (PSG), external connection of a radio module, service, communication with the test bed, FW update e. storage medium for example for read-out of detailed therapy data, programming by provider for the apparatus output, FW update/firmware update.

If there are fewer than five interfaces, preference should be given to groups a, c, d, e, while in the case of a ventilator having only three interfaces, at least groups c, d, e ought to be included. For some embodiments, a different preference of interface types may also be implemented here.

If the ventilator has for example two interfaces for wireless connection over a wide distance, for example an internal modem and an external modem, then that can be configured such that for example the internal modem is completely deactivated until the external modem has been removed and is no longer connected to the ventilator or part of the ventilator.

If the ventilator has wireless interfaces, for example, these should be able to be activated and deactivated individually, for example. In some embodiments, all other interfaces should be blocked when an input is effected via the user interface at the apparatus. Accordingly, the user interface thus always has the highest priority of all the interfaces. In some embodiments, the remaining interfaces likewise have a priority among one another. This priority is intended further to serve to ensure that only ever one interface is enabled for inputs, such as, for example, changes or data inputs at the apparatus. The other interfaces are thus blocked in the meantime. Independently of the enabling with regard to inputs, in some embodiments of the apparatus, it is possible for data to be read out at any time via at least two interfaces.

At the ventilator, the system is not necessarily set such that all data inputs via the interfaces that are not active at one time are blocked. By way of example, data from an external sensor or a diagnosis apparatus, etc., could continue to be input and written into the ventilator. This data input is intended also still to be able to take place while for example data inputs for setting a therapy are effected via the user interface. In this regard, here the system should merely prevent the blocking of a data input for data types which conflict with the data input via the interface having currently the highest priority.

The order of the priority can be permanently stored for example in the source code of the corresponding firmware. In specific cases, it is possible for the user on the part of the counterpart station at an interface of higher priority also to decide whether termination or interruption of the ongoing process, that is to say of the present data input via an interface of lower priority, is desirable and intended to be carried out.

In the case of a data input, the ventilator can also only be blocked vis à vis data inputs of other interfaces in such a way that only the constituent parts, for example combined in modules, which are affected by the data input are blocked. In this regard, it is possible for example nevertheless to effect data inputs via different interfaces simultaneously, just not for one constituent part or one module via two or more interfaces simultaneously.

In some instances, breathing into the mask can trigger e.g., the start of therapy, as a result of which e.g., a modem communication (wireless interface for large distances or else wired interface) is terminated in order to avoid an interaction of the radio radiation with the electronics of the apparatus or with the patient—or else in order to avoid an overloading of the controller with too many parallel tasks.

BRIEF DESCRIPTION OF THE DRAWINGS

The invention is explained in greater detail below by way of exemplary embodiments with reference to FIGS. 1 to 3, in which.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
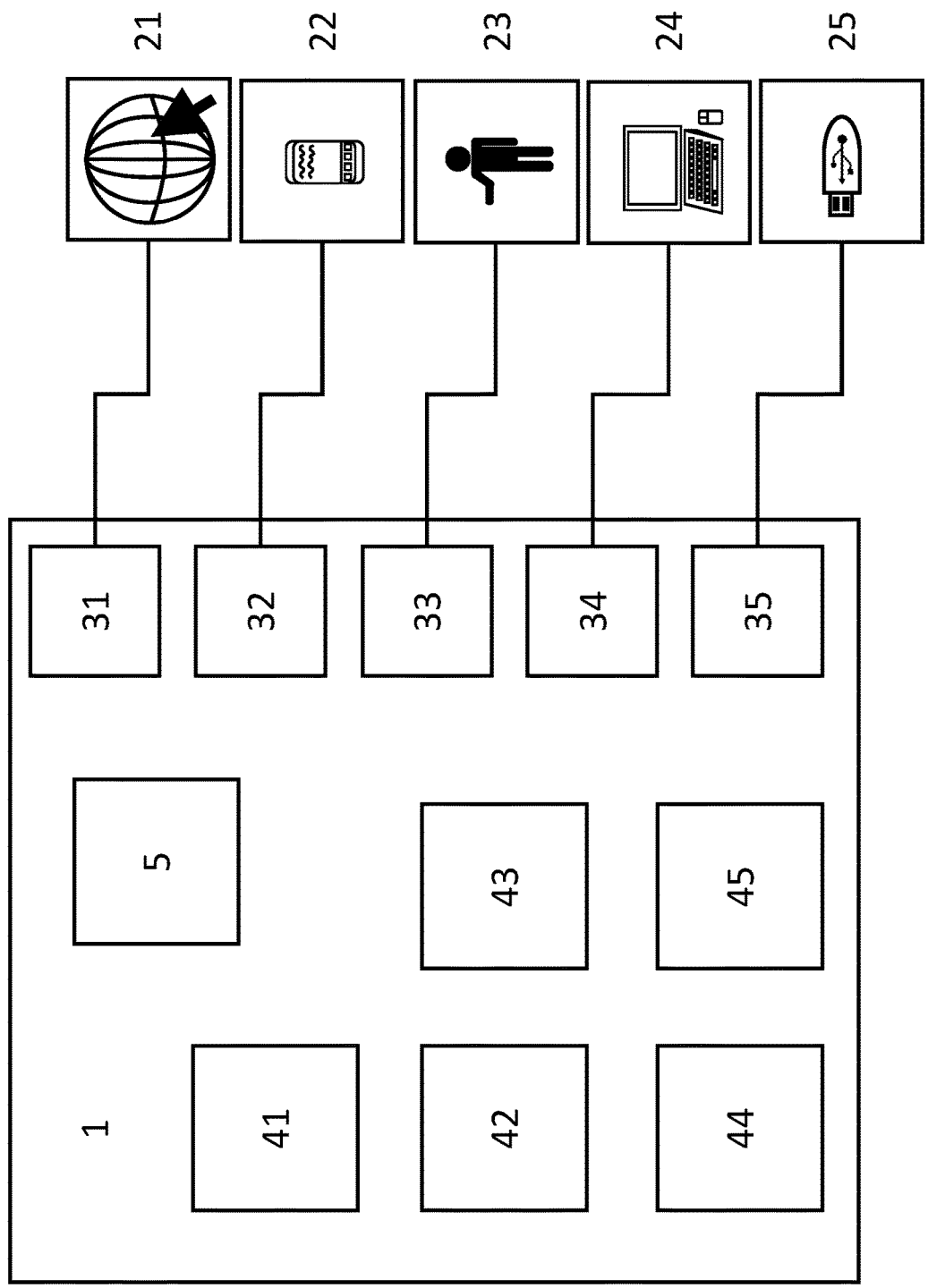
FIG. 1 shows an exemplary, schematic set-up of a ventilator 1 with the interfaces 31, 32, 33, 34, 35 and the modules 41, 42, 43, 44, 45.

FIG. 1 shows the exemplary, schematic set-up of a ventilator 1 with the interfaces 31, 32, 33, 34, 35 and the modules 41, 42, 43, 44, 45.

By way of example, module 41 is embodied as a fan and/or valve unit in order to generate a respiratory gas airflow for ventilation or therapy of a patient.

Module 42 is configured as a sensor unit, for example, which is able to detect measurement values, in particular parameters associated with a respiration flow rate, a respiration volume, a respiration frequency, a breathing in and breathing out duration, a respiration contour, a leakage or a therapy pressure. Optionally, the sensor unit 42 can carry out additional measurements of constituents or temperature of the respiratory gas or blood. The module 42 embodied as a sensor unit communicates the detected measurement values to the module 43 embodied as a conditioning unit, for example.

The module 43 embodied as a conditioning unit can condition the detected measurement values. By way of example, the conditioning unit can carry out smoothing, artefact correction or down-sampling of the measurement values. In some embodiments, the module 43 is also embodied as a combined conditioning, calculation and recognition unit. The calculation unit calculates, from the measurement values detected by the sensor unit and conditioning by the conditioning unit, signals and/or characteristic variables such as, for example, a mean, a medium, a percentile, a derivative, a frequency distribution, a duration or a proportion of over- or undershooting of threshold values. The recognition unit is configured to recognize events/states such as, for example, alarms, pauses in breathing, artefacts, coughs, oxygen (de)saturations, asynchrony between apparatus and user, breathing in, breathing out or mandatory breaths.

The module 44 is embodied for example as an internal storage unit and/or as a buffer storage unit which stores and/or respectively at least buffer-stores inter alia the values/parameters detected by the module 42 and/or the values, data and/or information conditioned by the module 43. Buffer storage means for example that the values, data and/or information are stored until transmission and are then erased or released for overwriting, for example.

The module 45 can be embodied as a monitoring unit, for example, which detects technical problems of the ventilator 1. Technical problems can be for example a low rechargeable battery level, faults in the electronics, a defect rechargeable battery, a defective component, a power failure, an incorrectly functioning accessory, an implausible measurement value or departure from an allowed temperature range. In the event of a technical problem having been recognized, the monitoring unit can display or communicate an alarm on the ventilator 1 via one of the interfaces. In some embodiments, these technical problems can in part also be regarded as serious faults which, in addition to a corresponding fault message on the display (user interface), block other data inputs and data outputs.

In further exemplary embodiments, the modules can furthermore be combined in module groups, wherein said module groups can indeed overlap. For illustration of how module groups can be handled, at this juncture the modules 41 and 42, the modules 42 and 43, and the modules 42 and 44 and 45 are combined to form a module group in each case, which are not illustrated more specifically in the drawings.

Furthermore, the ventilator has a control unit 5, which is connected to the interfaces 31, 32, 33, 34, 35 and the modules 41, 42, 43, 44, 45. The control unit 5 is configured inter alia to control the individual modules 41, 42, 43, 44, 45 and the interfaces 31, 32, 33, 34, 35 and optionally also to transfer data within the ventilator—between individual modules or else between modules and interfaces—or to enable and to control at least the communication between interface and module. For this purpose, the control unit 5 also has, or has access to, the priority assignment of the individual interfaces. Moreover, the control unit is configured to cause the ventilator 1 to transition to ongoing operation or to non-ongoing operation and/or to control this transition.

In this case, the interfaces are configured and designed such that they can set up connections to the remote counterpart stations 21 (Internet), 22 (smartphone), 23 (user), 24 (computer), 25 (USB stick). The interface 31 would be for example a wireless interface for large distances (here e.g. Wi-Fi/WLAN), the interface 32 would be a wireless interface for short distances (here e.g. Bluetooth), the interface 33 would be a user interface, the interface 34 would be a wired interface, and the interface 35 would be an interface for storage medium (here e.g. a USB interface).

The interface 31 is embodied for example as a wireless interface for large distances in order for example to set up a connection to the Internet 21. In this case, the connection to the Internet can be effected for example by way of mobile radio, a wireless network connection such as WLAN/Wi-Fi or for example via a cable modem.

The interface 32 is configured to set up a connection to a smartphone 22 via a WPAN, for example, such as Bluetooth, for example. Other devices such as, for example, a tablet PC or alternatively sensors with wireless connections are also conceivable for connection to wireless interfaces for short distances.

The interface 33 is configured for example as a user interface at the ventilator 1 and enables the communication with or connection to a user 23. The interface 33 can be embodied as a touch-sensitive screen (touchscreen), for example, which simultaneously enables the display or data output of data/information, etc., but also the data input. However, pushbutton, rotary and/or toggle switches would also be possible as user interface.

The interface 33 is configured for example to set up a connection to a computer 23, for example as a diagnosis tool. The interface 34 is configured for example to set up a connection to a building network 24—for example in a sleep laboratory or a hospital. The interface 35 is configured for example to set up a connection to the Internet 25. In this case, the connection to the Internet can be effected for example by way of mobile radio, a wireless network connection such as WLAN/Wi-Fi or via a cable modem, for example. The ventilator is configured and designed overall such that communication of all interfaces with all modules is possible. Communication of the interfaces among one another and of the modules among one another is also assumed as given. It should be pointed out that the ventilator 1 within the meaning of the invention can also have a larger or else smaller number of interfaces. The type of interfaces can also deviate from those mentioned here or else be additionally extended.

By way of example, the interfaces are assigned priorities based on the maximum or basic distance. Accordingly, the interface 33 is assigned the highest priority, inter alia since the interface 33 is embodied as a user interface directly at the ventilator. The next priority can be assigned to the interface 32 configured as a wireless interface for short distances. Following that the third highest priority is assigned to the interface 35. The interface 34 can be assigned a lower priority than the interface 33, but a higher priority than the interface 31. In the exemplary embodiment described, the interface 31 would thus acquire the lowest priority. Overall, therefore, the priority order from high to low priority results as follows: 33-32-35-34-31. The order of the priority can for example also be adapted manually or be effected on the basis of other criteria. In some embodiments, the priority of the interface 33 embodied as a user interface at the ventilator 1 is fixed as the highest priority.

Hereinafter some exemplary cases are intended to illustrate the method with respect to the effect of the allocated priority.

If a data input at module 41 by the user 23 takes place at the interface 33, for example, then at least at the module 41 no data input can take place or be begun via the interfaces 32, 31, 34 and 35. Firstly, this results from the fact that a data input at a module is intended to be possible only ever via one interface at the same time; secondly, the priority of the interface 33 also plays a part here. In this regard, by way of example, a data input via interfaces of lower priority is then only possible insofar as no data input via an interface of a higher priority is effected. By way of example, as a result of the data input, in addition the entire ventilator 1 can be blocked vis à vis data inputs via other interfaces or further data inputs via other interfaces can be blocked. Besides the blocking of data inputs via other interfaces, at the same time access generally—i.e. including read-out of data—can be blocked for some interfaces. Besides the blocking of individual modules or of the entire ventilator vis à vis further data inputs via other interfaces, module groups can also be blocked in principle. In the exemplary case described here of a data input at module 41 via interface 33, for example the module groups to which module 41 belongs can be blocked vis-à-vis data inputs via other interfaces—in the grouping presented further above, therefore, the module group including modules 41 and 42 would be blocked vis-à-vis data inputs. In some embodiments, under specific criteria, for example during an active therapy using the ventilator on a patient, data input and/or accesses to the ventilator via some interfaces can also generally be blocked. An example here would be an access via the interface 31, particularly if the interface 31 is designed as a wireless radio connection. In some embodiments, it is possible for this purpose to allocate a priority on the basis of the possible processor load or else possible burdening of the patient (for example as a result of radio radiation).

Furthermore, information or a message can be generated and displayed for the user 23 at the interface 33, for example if the intention is to be begin a data input via an interface having lower priority. If the modules or module groups affected by the data input are not blocked, said message can then be output for purely informative purposes. By way of example, if the ventilator 1 is generally blocked vis-à-vis data inputs via other interfaces, then a release possibility can also be displayed to the user 23 at the interface 33, such that for example individual modules are released for the data input via an interface of lower priority. In addition, it is also conceivable that messages can be generated and output via all other interfaces if a data input is currently being performed. Alternatively, however, such a message can also be output only via interfaces of higher priority.

If, in another case, for example, a data input at module 42 via interface 34 is performed by the computer 24, then for example a data input at least via the interface 31 is blocked as a result, since the latter interface is assigned a lower priority than the interface 34. As already described in the previous case, the blocking of a data input can be applicable at the level of the module, the module group or else for the entire ventilator 1. At the level of the module groups, in the case of a data input for module 42 and the module groups defined by way of example above, all module groups would be blocked since module 42 was assigned as part of all module groups. While a data input via the interface 31 is blocked, a data input via the interfaces 32, 33 and 35 may be possible, in principle, since these interfaces are assigned a higher priority. By way of example, if the smartphone 22 attempts to begin a data input via interface 32, then the data input being effected via interface 34 must firstly be terminated or interrupted. Depending on the data input, a certain time may be taken up until the process can be successfully interrupted or terminated. For some data inputs, it may additionally also hold true, for example, that they cannot in principle be interrupted or terminated. This is the case for firmware updates, for example, for which a termination may, inter alia, also result in malfunctions of the ventilator.

During, at the beginning and/or after the end of the data input via interface 34, a message or information regarding the data input can be output via the interface 33, for example. Particularly in the case of a message about the data input after the end of the data input, a summary of the change carried out can additionally be output in the message.

For some data inputs, a confirmation via the interface of highest priority or else via some other interface may additionally be required.

In some embodiments, the control unit 5 controls the blocking of the interfaces and/or the data inputs via the respective interface. If a data input via an interface is striven for or is intended to be begun—for example, a data input mode is started—the control unit, on the basis of the priority, decides whether the data input can be carried out. Moreover, the control unit 5 also controls the transition and the changeover from ongoing operation to non-ongoing operation, and vice versa. If a data input via an interface is intended to be begun, then the control unit 5 decides firstly whether the data input is possible during ongoing operation, whether the data input is not possible or whether the ventilator is changed over to non-ongoing operation in order to enable the data input. In the latter case, the control unit blocks the data input until the changeover from ongoing operation to non-ongoing operation has been concluded. This changeover can for example also comprise the storage of the data recorded during operation.

By way of some modules or constituent parts of the ventilator, such as, for example, by way of a monitoring unit or else the control unit, it is possible to check whether there are enough system resources and a reliable power supply to enable data inputs and data outputs in the first place. If there are not enough system resources available temporarily, for example because an encrypted data transfer is taking place, which ties up a high degree of processor capacities, then all other interfaces can be blocked for data inputs and data outputs for example by the control unit 5, optionally in association with data of the monitoring unit.

Figure 2:
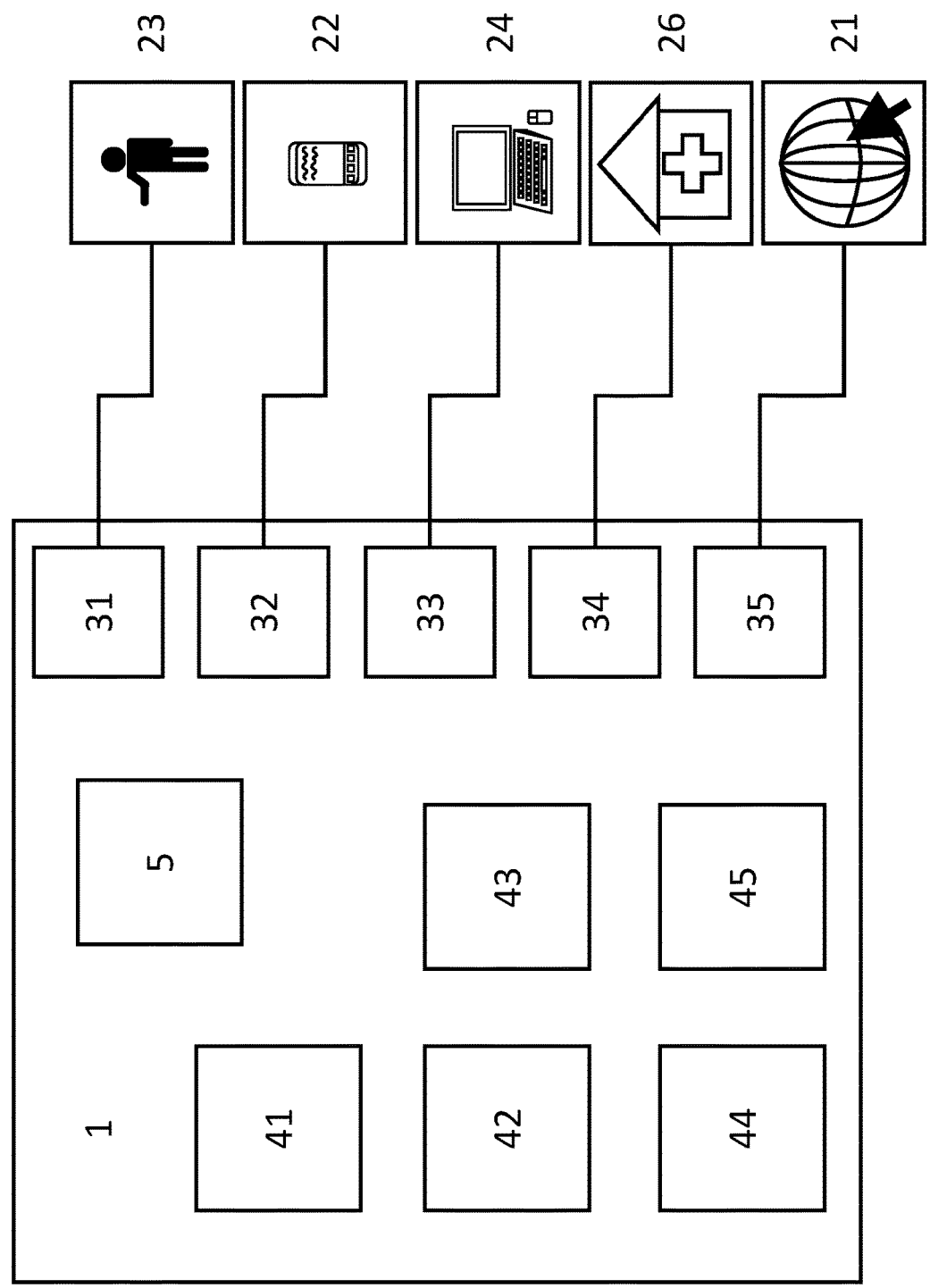
FIG. 2 shows another exemplary schematic set-up of a ventilator 1 with the interfaces 31, 32, 33, 34, 35 and the modules 41, 42, 43, 44, 45.

FIG. 2 shows another exemplary schematic set-up of a ventilator 1 with the interfaces 31, 32, 33, 34, 35 and the modules 41, 42, 43, 44, 45.

Furthermore, the ventilator has a control unit 5, which is connected to and communicates with the interfaces and the modules. For this purpose, the control unit 5 also has, or has access to, the priority assignment of the individual interfaces. In this case, the interfaces are configured and designed such that they can set up connections to the remote counterpart stations 23 (user), 22 (smartphone), 24 (computer), 26 (building network), 21 (Internet). In further exemplary embodiments, the modules can furthermore be combined in module groups, wherein said module groups can indeed overlap. For illustration of how module groups can be handled, at this juncture the modules 41 and 42, the modules 42 and 43, and the modules 42 and 44 and 45 are combined to form a module group in each case, which are not illustrated more specifically in the figures. The interface 31 is configured for example as a user interface at the ventilator 1 and enables communication with or connection to a user 23. The interface 32 is configured to set up a connection to a smartphone 22 via a WPAN, for example, such as Bluetooth, for example. The interface 33 is configured for example to set up a connection to a computer 24, for example as a diagnosis tool. The interface 34 is configured for example to set up a connection to a building network 26—for example in a sleep laboratory or a hospital. The interface 35 is configured for example to set up a connection to the Internet 21. In this case, the connection to the Internet can be effected for example by way of mobile radio, a wireless network connection such as WLAN/Wi-Fi or via a cable modem, for example. The ventilator is configured and designed overall such that communication of all interfaces with all modules is possible. Communication of the interfaces among one another and of the modules among one another is also assumed as given. It should be pointed out that the ventilator 1 within the meaning of the invention can also have a larger or else smaller number of interfaces. The type of interfaces can also deviate from those mentioned here or else be additionally extended.

By way of example, the interfaces are assigned priorities based on the maximum or basic distance. Accordingly, the interface 31 is assigned the highest priority, inter alia since the interface 31 is embodied as a user interface directly at the ventilator. The next priority can be assigned to the interface 32, following that the third highest priority is assigned to the interface 33. The interface 34 can be assigned a lower priority than the interface 33, but a higher priority than the interface 35. In the described exemplary embodiment, the interface 35 would thus acquire the lowest priority. Overall, therefore, the priority order from high to low priority results as follows: 31-32-33-34-35. The order of the priority can for example also be adapted manually or be effected on the basis of other criteria. In some embodiments, the priority of the interface 31 embodied as a user interface at the ventilator 1 is fixed as the highest priority.

Hereinafter some exemplary cases are intended to illustrate the method with respect to the effect of the allocated priority.

If a data input at module 41 by the user 23 takes place at the interface 31, for example, then at least at the module 41 no data input can take place or be begun via the interfaces 32, 33, 34 and 35. Firstly, this results from the fact that a data input at a module is intended to be possible only ever via one interface at the same time; secondly, the priority of the interface 31 also plays a part here. In this regard, by way of example, a data input via interfaces of lower priority is then only possible insofar as no data input via an interface of a higher priority is effected. By way of example, as a result of the data input, in addition the entire ventilator 1 can be blocked vis à vis data inputs via other interfaces or further data inputs via other interfaces can be blocked. Besides the blocking of data inputs via other interfaces, at the same time access generally—i.e., including read-out of data—can be blocked for some interfaces. Besides the blocking of individual modules or of the entire ventilator vis à vis further data inputs via other interfaces, module groups can also be blocked in principle. In the exemplary case described here of a data input at module 41 via interface 31, for example the module groups to which module 41 belongs can be blocked vis à vis data inputs via other interfaces—in the grouping presented further above, therefore, the module group including modules 41 and 42 would be blocked vis à vis data inputs. In some embodiments, under specific criteria, for example during an active therapy using the ventilator on a patient, data input and/or accesses to the ventilator via some interfaces can also generally be blocked. An example here would be an access via the interface 35, particularly if the interface 35 is designed as a wireless radio connection. In some embodiments, it is possible for this purpose to allocate a priority on the basis of the possible processor load or else possible burdening of the patient (for example as a result of radio radiation).

Furthermore, information or a message can be generated and displayed for the user 23 at the interface 31, for example if the intention is for a data input via an interface having lower priority to be begun. If the modules or module groups affected by the data input are not blocked, said message can then be output for purely informative purposes. By way of example, if the ventilator 1 is generally blocked vis à vis data inputs via other interfaces, then a release possibility can also be displayed to the user 23 at the interface 31, such that for example individual modules are released for the data input via an interface of lower priority. In addition, it is also conceivable that messages can be generated and output via all other interfaces if a data input is currently being performed. Alternatively, however, such a message can also be output only via interfaces of higher priority.

If, in another case, for example, a data input at module 42 via interface 33 is performed by the computer 24, then for example a data input at least via the interfaces 34 and 35 is blocked as a result, since the latter interfaces are assigned a lower priority than the interface 33. As already described in the previous case, the blocking of a data input can be applicable at the level of the module, the module group or else for the entire ventilator 1. At the level of the module groups, in the case of a data input for module 42 and the module groups defined by way of example above, all module groups would be blocked since module 42 was assigned as part of all module groups. While a data input via the interfaces 34 and 35 is blocked, a data input via the interfaces 32 and 31 may be possible, in principle, since these interfaces are assigned a higher priority. By way of example, if the smartphone 22 attempts to begin a data input via interface 32, then the data input being effected via interface 33 must firstly be terminated or interrupted. Depending on the data input, a certain time may be taken up until the process can be successfully interrupted or terminated. For some data inputs, it may additionally also hold true, for example, that they cannot in principle be interrupted or terminated. This is the case for firmware updates, for example, for which a termination may, inter alia, also result in malfunctions of the ventilator.

During, at the beginning and/or after the end of the data input via interface 33, a message or information regarding the data input can be output via the interface 31, for example. Particularly in the case of a message about the data input after the end of the data input, a summary of the change carried out can additionally be output in the message.

For some data inputs, a confirmation via the interface of highest priority or else via some other interface may additionally be required.

Figure 3:
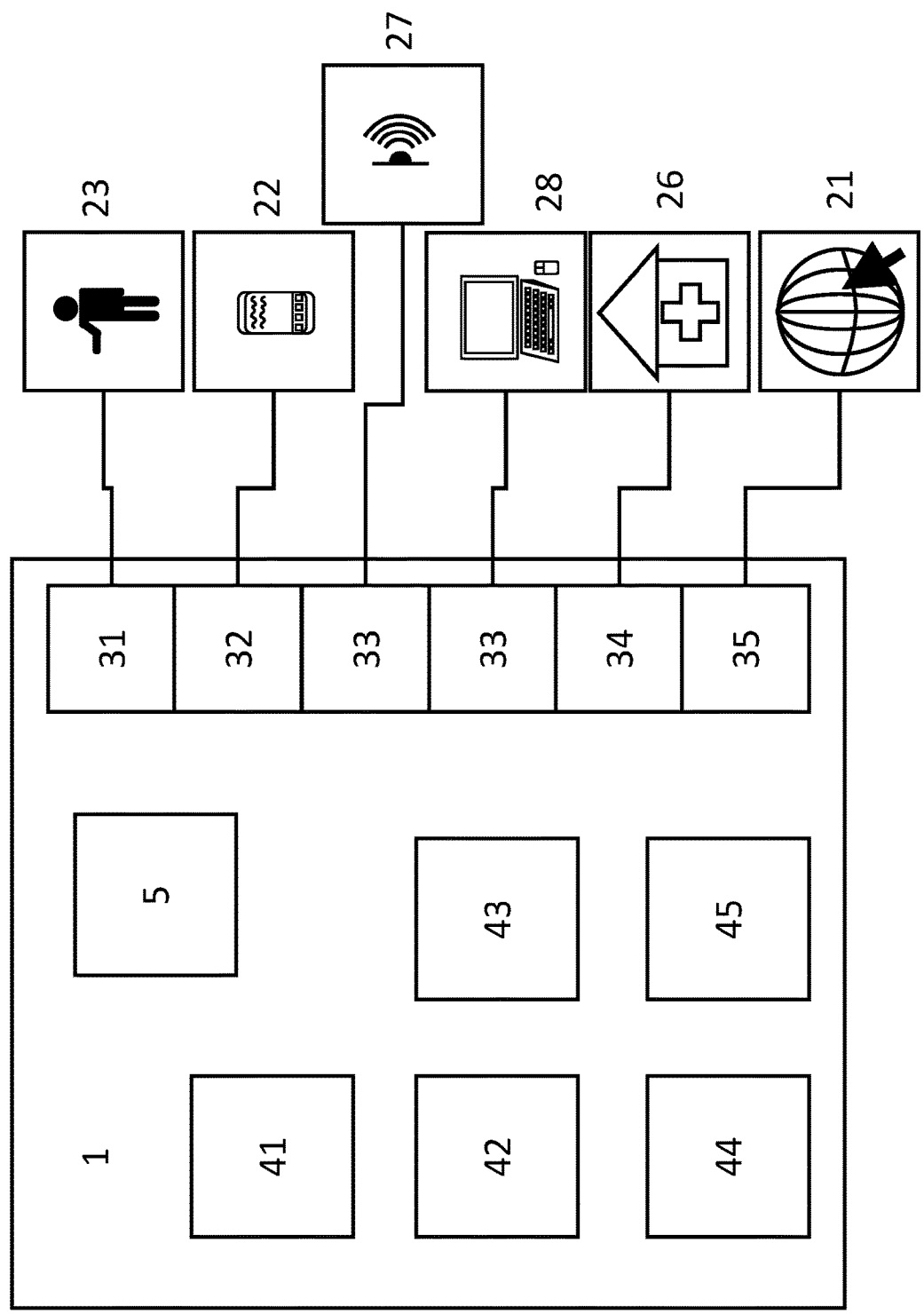
FIG. 3 shows an exemplary embodiment of the ventilator 1, which largely corresponds to that from FIG. 1 but has two interfaces 33.

FIG. 3 illustrates an exemplary embodiment of the ventilator 1, which largely corresponds to that from FIG. 1. In contrast to the ventilator 1 from FIG. 1, the ventilator 1 in FIG. 3 has two interfaces 33. These interfaces 33 are of the same type and would acquire the same standing in a fixed priority list, for example, that is to say would be assigned the same priority. The interfaces 33 are configured for example such that, inter alia, a sensor 27 and a service apparatus 28 can be connected to the ventilator 1 via said interfaces. Since both interfaces 33 are of the same type, the interfaces 33 are thus also interchangeable, that is to say that both sensor 27 and service apparatus 28 can be connected to each of the two interfaces 33. Even if the interfaces 33 are both assigned the same priority, it may nevertheless be the case that at times the service apparatus 28 must be the counterpart station having the highest priority or else must be able to perform data inputs outside the priority assignments, i.e., in this respect should also be above the priority of the interface of highest priority—interface 31 in this exemplary embodiment. For this case, firstly a dynamic priority can be introduced, according to which for example besides the pure interface, the connected counterpart station is also concomitantly incorporated in the priority. According to this dynamic priority allocation, by way of example, one of the interfaces 33, upon connection to service apparatus 28, is automatically assigned a high or the highest priority. Thus, if a data input via interface 33 is then effected by the service apparatus 28, as a result the data input via the other interfaces is blocked by the control unit 5 or at least blocked for constituent parts or modules affected by the data input by the service apparatus 28. In some embodiments, the data input by the sensor 27 or similar apparatuses, such as diagnosis apparatuses, for example, can in principle be excluded from the blocking. By way of example, a decision can be taken here about the type of data input. In this case, for example, sensor data can be handled differently than data inputs for the configuration of therapy measures. The regulation by way of different data input modes can also be used here. In this regard, the sensor 26 starts a data input mode which comprises only the data input of sensor data. This data input mode can be set such that, rather than sensor data generally, for example only specific sensor data are also encompassed. In this regard, even further sensors can also be connected to the ventilator, which sensors input other sensor data and for this purpose likewise start additional data input modes. By way of the blocking of data input types or else through the use of data input modes, what can thus also be achieved is that data inputs via different interfaces at the same time are possible, but by virtue of the fact that data input types or data input modes already taken are blocked, no data inputs can conflict. Furthermore, it is also conceivable, for example, for specific data inputs nevertheless to block a plurality of data input modes or types. For example, as a result of the transfer of a firmware update via interface 33 by the service apparatus 28, further data inputs can initially be blocked in order not to jeopardize the success of the update. Conversely, the system can for example also be configured such that specific actions of the ventilator 1, for example the beginning of a therapy, block some data inputs or data input modes for all interfaces. A data input in the form of a firmware update can thus be prevented or blocked for example while a therapy is being carried out. These blocks can for example be fixedly preset or else be sent together with the respective data inputs by means of a marking or the like, such that for example the control unit recognizes whether a data input is permitted to be terminated or which data inputs are permitted to be effected in parallel.

Instead of or else in addition to the dynamic allocation of priorities to the interfaces, bridging or circumventing of the priorities by specific input modes or combinations of interfaces and counterpart stations can also be provided. In this regard, for example, a service apparatus 28, upon connection to interface 33, can circumvent or bridge the priorities and thus also effect data inputs and in so doing block all other interfaces, independently of the (envisaged) priority. Formally, the interface 33 connected to the service apparatus 28 is thus set to the highest priority. In this case, this procedure can also be applied to any desired combinations of interfaces and counterpart stations.

Moreover, one of the interfaces 31, 32, 33, 34, 35 can be embodied as a USB interface or an interface for SD cards to which a low priority is assigned. In some cases, the counterpart stations connected to such interfaces can contain master configurations, for example, which are intended to be transferred to the ventilator 1. During the transfer, that is to say the data input via e.g. the SD card or USB interface, the intention is for no other data inputs to be possible or for at least the data input via the SD card or USB interface to be assigned the highest priority. This can be achieved for example by the priority assignment being circumvented, i.e., the SD card or USB interface being assigned the highest priority in an irregular fashion. Various methods are conceivable as triggers for circumventing the priority assignment. By way of example, a code which starts the circumvention of the priority assignment or requests the highest priority can be transferred via the corresponding counterpoint station, e.g., a USB stick. Moreover, a confirmation or action via the user interface 31 or some other interface can have the consequence that the priority assignment is intended to be circumvented, or is circumvented, by the SD card or USB interface. For instance, by way of the user interface, for example, it is possible to indicate that a USB stick or an SD card with a master configuration has been connected to the ventilator 1 and a data input via the SD card or USB interface is to be started. If this is confirmed, then the data input via the SD card or USB interface is begun and the other interfaces are blocked at least partly for data inputs.

Moreover, the control unit 5 can be configured such that it checks the data held on the storage medium (USB stick, SD card) and, on the basis of the content, decides whether a temporary high priority is provided for the interface or the priority assignment is circumvented.

LIST OF REFERENCE CHARACTERS

1 Ventilator
5 Control unit
21 Internet
22 Smartphone
23 User
24 Computer
25 USB stick
26 Building network
27 Sensor
28 Service apparatus
31 Interface
32 Interface
33 Interface
34 Interface
35 Interface
41 Module
42 Module
43 Module
44 Module
45 Module

What is claimed is:

1. A method for managing a data exchange via at least three interfaces of a ventilator, wherein the method comprises configuring at least one interface of the at least three interfaces for a data exchange with at least one counterpart station that is spatially separate from the ventilator, the data exchange comprising a data input and a data output, and a data output and/or data input is possible during an ongoing operation of the ventilator via at least one of the at least three interfaces only if sufficient system resources and a reliable power supply are available.

2. The method of claim 1, wherein a reliable power supply is present if the ventilator is connected to a sufficiently charged rechargeable battery whose sufficient charge depends upon type, duration and interface for data output and/or data input.

3. The method of claim 2, wherein a sufficient charge of the rechargeable battery is more than 5% of its maximum charge.

4. The method of claim 2, wherein a sufficient charge of the rechargeable battery is determined to be more than 10% of its maximum charge.

5. The method of claim 2, wherein a sufficient charge of the rechargeable battery is more than 50% of its maximum charge.

6. The method of claim 1, wherein system resources which must be sufficient comprise processor capacity and main memory.

7. The method of claim 1, wherein in the case of insufficient system resources for a data transfer the data transfer is delayed and is carried out at a later point in time when the system resources are sufficient for the data transfer.

8. The method of claim 1, wherein a data input via one of the at least three interfaces blocks the data input via at least one other of the at least three interfaces.

9. The method of claim 1, wherein a priority is assigned to the at least three interfaces and the data input via an interface with higher priority blocks the data input via at least one interface of lower priority.

10. The method of claim 1, wherein the data input via at least one interface of lower priority of the at least three interfaces is blocked if the data input via interfaces of lower priority conflicts with the data input via an interface of higher priority of the at least three interfaces.

11. The method of claim 1, wherein at least three of groups a to e are represented by said at least three interfaces:
   a. Wireless interfaces for large distances
   b. Wireless interfaces for small distances
   c. User interface
   d. Wired interfaces
   e. Interfaces for a storage medium.

12. The method of claim 1, wherein wireless interfaces of the ventilator can be activated and deactivated and one of the at least three interfaces is a user interface at the ventilator, the user interface being assigned a highest priority with regard to the data input.

13. The method of claim 1, wherein for data input purposes a data input mode is started and starting of the data input mode via one interface blocks starting of a data input mode via the other interfaces of the at least three interfaces, wherein different data input modes are in each case started for different data inputs, wherein starting of a data input mode via one interface blocks starting of the same data input mode by at least one other interface of lower priority and/or starting of a data input mode for a data input via other interfaces is blocked if the data input mode to be started via interfaces of lower priority conflicts with the data input mode of the data input via interfaces of higher priority.

14. The method of claim 1, wherein the data input via an interface is interrupted and/or terminated by a beginning of a data input by an interface to which a higher priority is assigned, specific data inputs being not interrupted and/or terminated regardless of a priority of the interface via which the data input is effected.

15. The method of claim 1, wherein an activation of functions and/or modes of operation of the ventilator block the data exchange via at least one interface and/or deactivates at least one interface until an end of the function and/or mode of operation.

16. The method of claim 1, wherein priority is automatically assigned to the interfaces, and the priority of the interfaces can be varied manually at the ventilator, the priority of the interfaces being allocated differently at least for ongoing operation and non-ongoing operation.

17. The method of claim 1, wherein the ventilator transitions from ongoing operation to non-ongoing operation as soon as a connection via a USB interface is established, and a data input via all other interfaces is blocked when a connection via the USB interface is established.

18. A ventilator, wherein the ventilator comprises at least three interfaces for a data exchange, at least one interface being configured for a data exchange with at least one counterpart station that is spatially separate from the ventilator, the data exchange comprising a data input and a data output, and wherein the ventilator is configured such that a data output and/or data input is possible during an ongoing operation of the ventilator via at least one of the at least three interfaces only if sufficient system resources and a reliable power supply are available.

19. The ventilator of claim 18, wherein a priority is assigned to the at least three interfaces and the data input via an interface with higher priority blocks the data input via at least one interface of lower priority.

20. The method of claim 1, wherein a reliable power supply is present if the ventilator is connected to an electrical grid.

* * * * *